US005614412A

United States Patent [19]
Smith et al.

[11] Patent Number: 5,614,412
[45] Date of Patent: Mar. 25, 1997

[54] APPARATUS FOR CARRYING FLEXIBLE CONTAINERS AND METHOD OF TRANSFERRING FLUIDS TO CONTAINERS

[76] Inventors: Stephen L. Smith, 510 E. Mayfair Rd., Arlington Heights, Ill. 60005; James Bender, 565 Whitebirch Rd., Lindenhurst, Ill. 60046; Jeffrey Martinson, 526 Banbury, Mundelein, Ill. 60060; Maureen Loudovaris, 114 Mainsail Dr., Grayslake, Ill. 60030; Orrin D. Mitsven, Jr., 37125 N. Antonio Ave., Lake Villa, Ill. 60046; Kristen L. Unverzagt, 243 N. Plum Grove Rd., Palatine, Ill. 60067

[21] Appl. No.: 526,034

[22] Filed: Sep. 8, 1995

[51] Int. Cl.$^{6}$ .................................................. C12M 3/00

[52] U.S. Cl. ........................ 435/305.1; 435/809; 211/191

[58] Field of Search ............................. 435/304.1, 305.1, 435/809; 211/13, 40, 191

[56] References Cited

U.S. PATENT DOCUMENTS

| | | | |
|---|---|---|---|
| 1,017,369 | 2/1912 | Bates . | |
| 2,176,613 | 10/1939 | Rygaard | 226/93 |
| 2,606,704 | 8/1952 | Nichols | 226/20.6 |
| 2,830,396 | 4/1958 | Gowland | 41/5 |
| 3,576,721 | 8/1968 | Mason | 435/809 |
| 3,635,350 | 1/1972 | Wolf | 211/40 |
| 4,237,096 | 12/1980 | Popoff et al. | 422/102 |
| 4,625,494 | 12/1986 | Iwatschenko et al. | 53/432 |
| 4,720,463 | 1/1988 | Farber et al. | 435/291 |
| 4,810,241 | 3/1989 | Rogers | 604/28 |
| 4,823,833 | 4/1989 | Hogan et al. | 137/567 |
| 4,937,194 | 6/1990 | Pattillo et al. | 435/240.2 |
| 4,972,886 | 11/1990 | Bernstein | 141/98 |
| 4,981,144 | 1/1991 | Carels, Jr. | 128/760 |
| 5,092,378 | 3/1992 | Dunham | 141/237 |
| 5,240,854 | 8/1993 | Berry et al. | 438/284 |
| 5,261,466 | 11/1993 | Koyanagi | 141/10 |
| 5,293,757 | 3/1994 | Nishio | 62/344 |
| 5,357,733 | 10/1994 | Weikert | 53/455 |

OTHER PUBLICATIONS

Operator's Manual from Fenwal Laboratories, Division of Travenol Laboratories, Inc., for FENWAL® Solution Transfer Pump, Apr. 1987.

*Primary Examiner*—David A. Redding
*Attorney, Agent, or Firm*—Wallenstein & Wagner, Ltd.

[57] ABSTRACT

The present invention provides an apparatus for holding and carrying a plurality of flexible medical containers. The carrier has a rack having a plurality of plates positioned in parallel spaced relation, the plates defining a chamber between each pair of adjacent plates. A plurality of spacer assemblies each extend through the rack to connect the plates and to maintain their spaced relationship. The spacer assemblies are spaced along marginal edges of the rack to define two opposed end walls, a bottom, and an opening to the rack to allow access to each of the chambers. A flange extends from one of the plates and has a hole that allows the carrier to be suspended. The invention further provides for a system for transferring fluids and a method for mixing solutions using the carrier.

8 Claims, 2 Drawing Sheets

APPARATUS FOR CARRYING FLEXIBLE CONTAINERS AND METHOD OF TRANSFERRING FLUIDS TO CONTAINERS

TECHNICAL FIELD

This invention relates to a carrier for containing fluid containers and more specifically to a carrier for containing flexible plastic fluid containers.

BACKGROUND ART

Flexible plastic containers are commonly used in the medical field for a wide variety of applications such as to store and deliver therapeutic fluids to a patient or to contain cells that are being grown in a cell culture medium. The plastic containers typically have a front and rear panel that are sealed along their lateral edges to define an aseptically sealed containment pouch. Access is typically provided to the containment pouch through a fluid conduit such as tubing that extends from outside the containment pouch to interior of the containment pouch. The tubing is sealed with a membrane or elastomeric septum to maintain a sterile environment. On a side of the container opposite of the access tubing is a hanger hole so that the hanger may be suspended from a hanger or a load cell.

It is possible to grow suspension cells (anchorage-independent cells) or adherent cells (anchorage-dependent cells), in vitro, in flexible plastic containers such as those disclosed in commonly assigned U.S. patent application Ser. No. 08/330,717. The cells are grown in a cell culture medium contained within the flexible container and the container is placed inside an incubator. It is possible to use aliquots taken from a container of cultured cells to start numerous other cell cultures. This process, known as cell subculturing, increases the rate of growth of the cells.

Cell subculturing requires transferring an aliquot of the cultured cells contained within one container to a receiving container or numerous receiving containers and diluting the aliquot of cultured cells in each receiving container with a cell growth medium. The cell growth medium provides the necessary nutrients for the cells to grow. A method and apparatus for subculturing cells is disclosed in commonly assigned U.S. Pat. No. 4,937,194 ("'194 Patent"). The '194 Patent discloses fluidly connecting in series a cell culture container to a container having cell culture medium and eventually to a receiving, container or numerous receiving containers. The '194 Patent discloses using a metering device including, for example, a burette (FIG. 1), a roller pump (FIG. 2), a container having a fixed volume, or a syringe (FIGS. 3 and 4) to provide the desired amount of cell growth medium to dilute the aliquot of cell culture.

While the '194 Patent discloses a method and apparatus for aseptically connecting a cell culture container to multiple receiving containers, the metering device and method used are labor intensive and require continued operator attention.

U.S. Pat. No. 5,240,854 ("the '854 Patent") also discloses a device and method for the subculturing of cells. The device includes an array of growth chambers enclosed within a vessel. The growth chambers are defined by an array of stacked plates having a peripheral wall. The plates are welded together along the peripheral walls of one plate to a groove in another plate by ultrasonic welding or solvent bonding or other technique to form a fluid tight seal between the plates. The stacked plates form cell Growth surfaces. Cell culture and cell growth media are supplied and removed from the plates through an inlet fluid conduit and manifold and an outlet fluid conduit and manifold.

Because the '854 Patent requires that the cell growth plates be welded together, it makes access to the cells difficult as one has to cut open the vessel to inspect the cells. (Col. 8, lines 52–55). Further, because the plates are housed in a vessel, they are apparently not subject to visual inspection through a microscope or the naked eye.

Other methods for subculturing cells requires a solution transfer pump to transfer the desired amounts of the cell culture and cell culture medium to a single receiving container. A solution transfer pump typically has numerous rotors each rotor having a separate fluid inlet that may be connected to separate containers. The solution transfer pump is capable of transferring fluids either simultaneously or sequentially from these separate containers to a single receiving container. In particular for cell subculturing, a cell culture container and a container of cell growth medium are connected to separate pump rotor inlets. A receiving container is fluidly and aseptically connected to an outlet side of the solution transfer pump. To transfer the desired volume of the cell culture and the growth medium, the receiving container is suspended from a load cell on the solution transfer pump which allows the volume of liquid transferred to the receiving container to be determined gravimetrically.

Using a solution transfer pump in this fashion provides several disadvantages. Only one receiving container may be hung from the load cell and thus only one receiving container may be connected to the solution transfer pump. Thus, in instances where a cell culture is to be divided into numerous receiving containers, each fill operation requires an operator to form an aseptic seal upon attaching and detaching the receiving container to the outlet of the transfer pump. This is a time consuming process which, in many instances, takes longer than the time required to transfer fluids to the receiving container. Further, each seal operation presents the risk of contaminating the cell culture.

Each of these filled receiving containers must then be immediately transferred to an incubator to continue the cell culture process. Thus, multiple trips must be made in transporting the filled receiving container to the incubator which increases the possibility that one of these containers may be damaged by dropping it or otherwise. Each trip to the incubator also increases the time to complete the subculture process. Minimizing the fill time is critical to the viability of the cell culture supply as the cell culture supply is outside the incubator and exposed to outside environment temperatures and potential contaminants.

Using a receiving container as described above having an access tube on one end of the container and a hanger on the opposite end creates further problems when used with a solution transfer pump. Because the container is suspended from the hanger to the load cell, the access tubing is necessarily on the bottom of the container. Thus, the solution transfer pump must fill the container from the bottom up. This increases the back pressure on the pump as the pump has to force fluid upward against the force of gravity and against the fluid in the container. Filling from the bottom up may also lead to uneven filling of the container.

In accordance with the present invention an apparatus, system and method of transferring fluids from one or more containers to numerous containers are provided using a solution transfer pump. The invention is particularly useful for fill operations such as the subculturing of cells and hospital pharmacy fill operations, where the fluid transfer must be performed aseptically. The invention when used for the subculturing of cells should decrease the number of cultures lost due to a break in aseptic conditions and should decrease the time required to complete a fill operation.

DISCLOSURE OF INVENTION

The present invention provides an apparatus for holding and carrying a plurality of flexible medical containers. The apparatus, which will be referred to as a carrier, has a rack of a plurality of plates positioned in parallel spaced relation. The plates define a chamber between each pair of adjacent plates. The carrier has a plurality of spacer assemblies each extending through the rack to connect the plates and to maintain the spaced relationship of the plates. The spacer assemblies are spaced along marginal edges of the rack to define two opposed end walls, a bottom, and an opening to the rack to allow access to each of the chambers. The carrier has a hook connected to or integral with a plate for carrying and suspending the carrier.

Preferably the rack has 5 plates defining 4 chambers each chamber being capable of receiving a flexible medical container. It is also preferred that the plates are generally rectangular in shape, have marginal edges that are in registration, and have a series of bores through the plates to lighten the carrier and to allow for air to flow through the plates.

It is a further object of the present invention to provide a system for transferring fluids from one and preferably at least two separately contained fluid sources to a plurality of receiving containers using a solution transfer pump. In particular, the solution transfer pump has a fluid inlet and a fluid outlet and is capable of connecting to the two fluid sources at the fluid inlet. The above described carrier is removably attached to the pump and holds a plurality of flexible receiving containers. Each of the flexible receiving containers are connectable to the fluid outlet of the pump with a fluid passageway. The pump is capable of transferring fluid from each of the separately contained fluid sources to each of the flexible receiving containers. Preferably, the receiving containers have an access flow path, such as a port tubing that allows for filling the bag from the top of the container.

It is a further object of the present invention to provide a method for mixing solutions comprising the steps of providing a first container having a first solution, and a second container having a second solution. Further providing a solution transfer pump having a fluid inlet and a fluid outlet, and a rack having a plurality of plates positioned in parallel spaced relation defining a chamber between each pair of adjacent plates. Further providing a plurality of receiving containers and positioning one of each of these containers inside each chamber. The method further includes connecting the first and the second container to the fluid inlet of the pump, connecting each of the receiving containers to the outlet of the pump, pumping solution from each of the first container and the second container to each of the receiving containers to establish a desired concentration of each first and second solution in each of the receiving containers and a desired volume in each of the receiving containers.

BEST MODE FOR CARRYING OUT THE INVENTION

Figure 1:
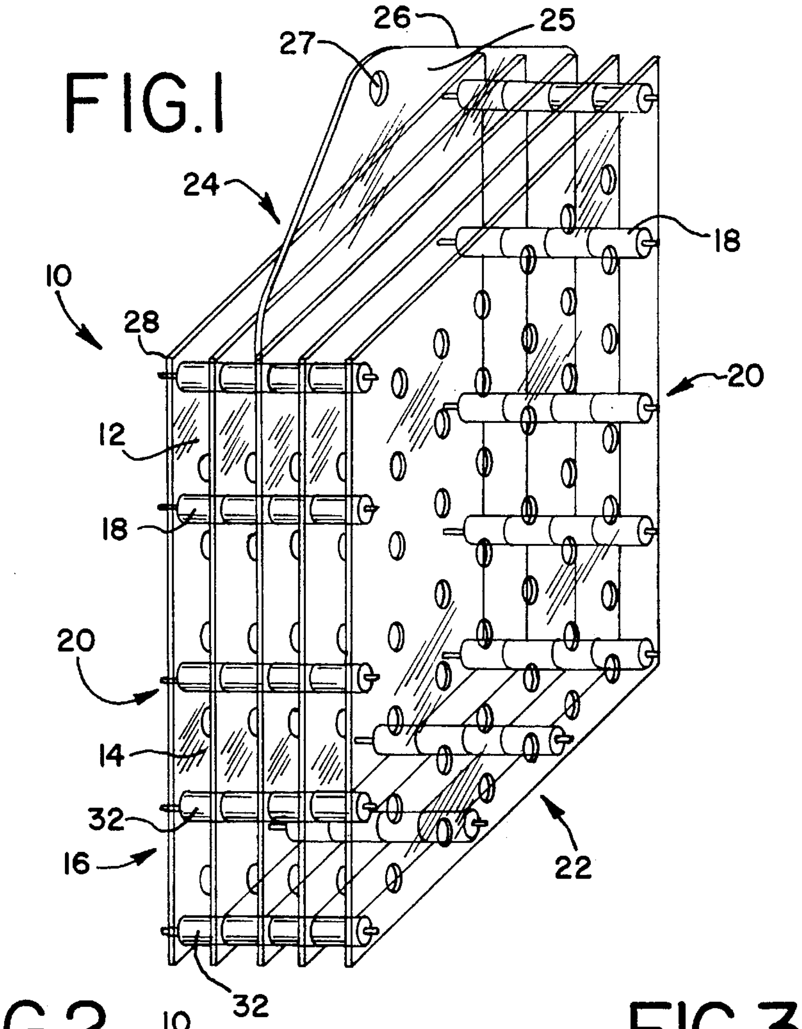
FIG. 1 is a perspective view of a carrier for flexible containers of the present invention.
Figure 2:
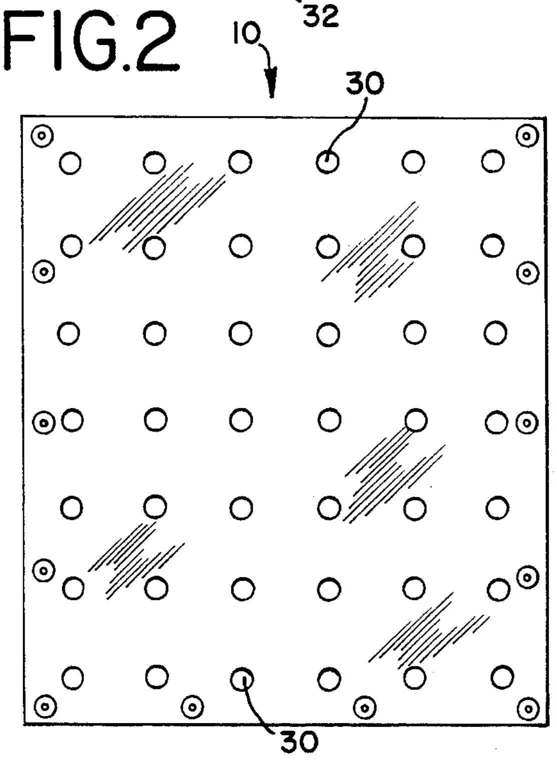
FIG. 2 is a front view of the carrier for flexible containers.
Figure 3:
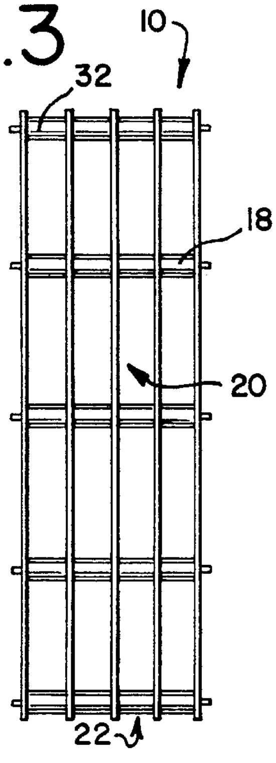
FIG. 3 is a side view of the flexible container carrier.

While the invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

Figure 4:
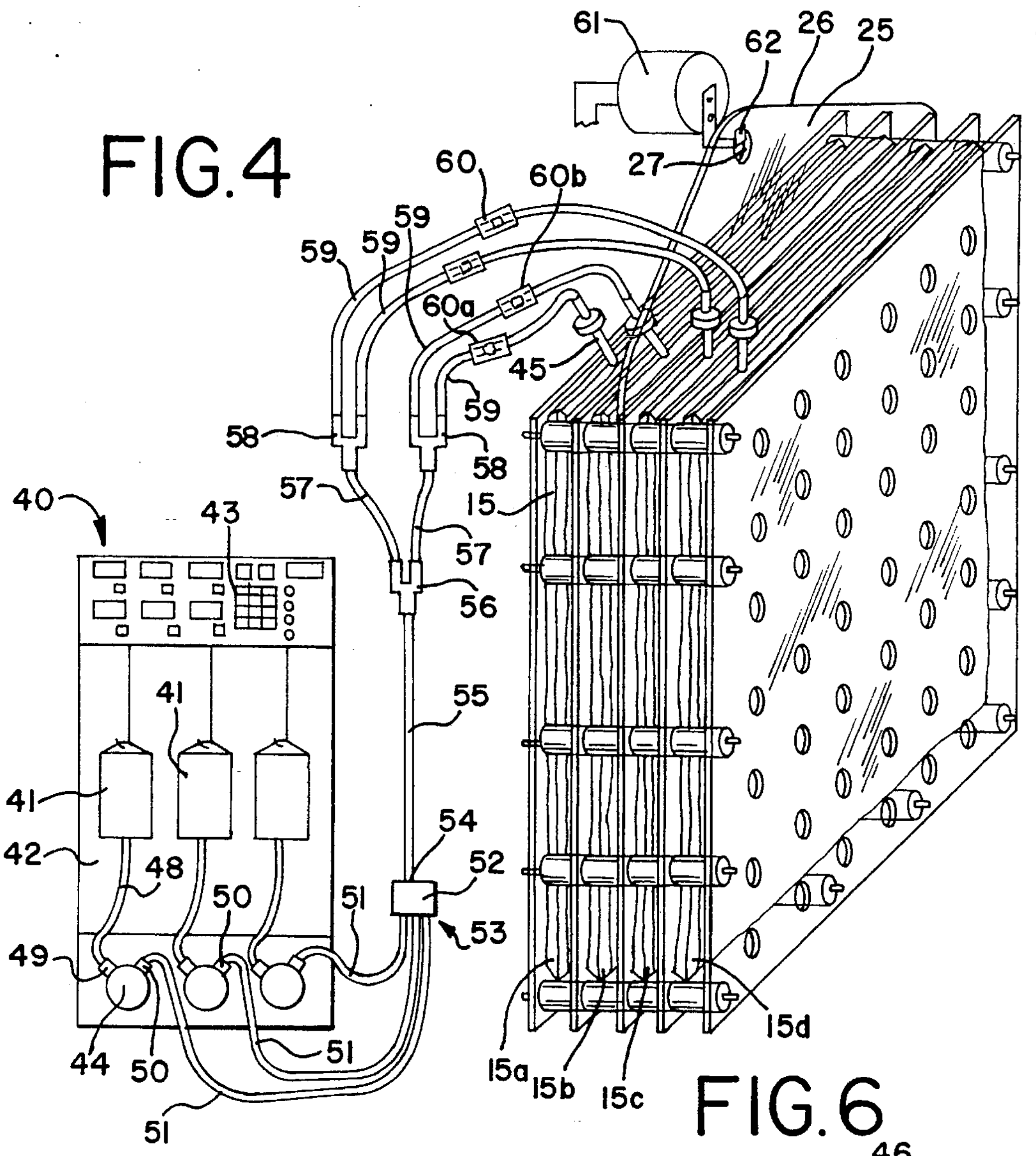
FIG. 4 is a schematic view of a solution transfer pump and the flexible container carrier.
Figure 5:
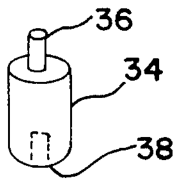
FIG. 5 is a front view of a spacer subassembly.

FIG. 1 shows a carrier 10 for flexible containers having a plurality of plates 12 mounted in parallel spaced relationship defining a chamber 14 between each adjacent plate. As will be discussed in greater detail below, each of the chambers 14 will hold a flexible medical container 15 (FIGS. 4 and 5). The stack of plates 12 defines a rack 16. A series of spacer assemblies 18 extend through the rack 16 to connect the plates 12 and to maintain the spaced relationship of the plates 12. The spacer assemblies 18 are spaced along marginal edges of the rack 16 to define two opposed end walls 20, a bottom wall 22, and an opening 24 to the rack 16 to allow access to each of the chambers 14. One of the plates may have a flange 25 that extends beyond the other plates 12. The flange 25 has lateral edges that taper 26 inwardly and upwardly. The flange 25 has a centrally located hole 27 for suspending the carrier 10 on a hook or load cell arm as described below.

Preferably, the rack 16 has five plates 12 defining four chambers. However, any number of plates may be used without departing from the invention. The plates 12 have a generally rectangular shape and are mounted so that the marginal edges of the plates are in registration. However, it is contemplated by the present invention that the plates 12 could have a different geometric shape or be mounted out of registration without departing from the present invention. It is also contemplated that the corners 28 of the plates 12 may be radiused or that the marginal edges of the plates 12 may be beveled or tapered.

It is also preferred that the plates 12 have a series of spaced bores 30 which serve to lighten the carrier 10 and allow for the passage of air, which is important for the subculturing of cells. The plates 12 and the spacer assemblies 18 should be fabricated from a rigid, light material such as a polycarbonate as sold under the trademark LEXAN®. However, it is contemplated that the plates 12, and the spacer assemblies 18 could be fabricated from other polymer based compositions, metals, alloys or other materials without departing from the present invention.

The plates 12 and the spacer assemblies 18 should be dimensioned to accommodate the flexible container 15. The carrier 10 may be dimensioned to accommodate any sized flexible container. However the carrier 10 will most typically be used to hold flexible containers within a range of 3,000 ml–20 ml capacity. For example a cell culture bag of 3000 ml volume has dimensions of 14 inches ×8.5 inches. Each plate 12 of the carrier 10 to hold such a 3000 ml bag would have the dimensions of approximately 14.5 inches× 9.5 inches. Each chamber 14 has a 1 inch height which provides sufficient space for typical bag filling volume. The plates 12 each have a thickness of ⅛ inch. The carrier 10 is 4.5 inches deep.

The spacer assemblies 18 preferably have a plurality of subassemblies 32 that extend between adjacent plates 12 and are connected together in an end-to-end-fashion through a hole in the plate 12. Preferably, the subassemblies have, as is shown in FIG. 5, a riser 34 having a male end 36 and a female end 38 so that the subassemblies 32 may be snap fit together. This provides for ease of construction so that a carrier 10 having any number of plates may be assembled or disassembled quickly and without using hand tools. In addition to adding modular functionality, it allows for separate sterilization of individual components such as by autoclaving.

The subassemblies 32 also could consist of a series of cylindrical spacers each having a bore therethrough wherein the bores are aligned with one another and a hole in the plate 12 and a threaded rod is passed therethrough and fastened with a nut at one end.

The receiving containers may be made of any flexible material and preferably polymer based materials including polyvinyl chloride. The receiving container 15 for the subculturing of cells must be optimized for a given cell type, and be controlled for at least two parameters: (1) partial pressure of oxygen ($pO_2$) to serve the aerobic needs of the cells, and (2) partial pressure of carbon dioxide ($pCO_2$) to maintain the pH of the growth medium. Such containers are described in U.S. Pat. Nos. Re. 31,135; 4,140,162, and in the copending and commonly assigned U.S. Pat. Ser. No. 08/330,717 which discloses a flexible container having a solution contact layer or high impact polystyrene.

Figure 6:
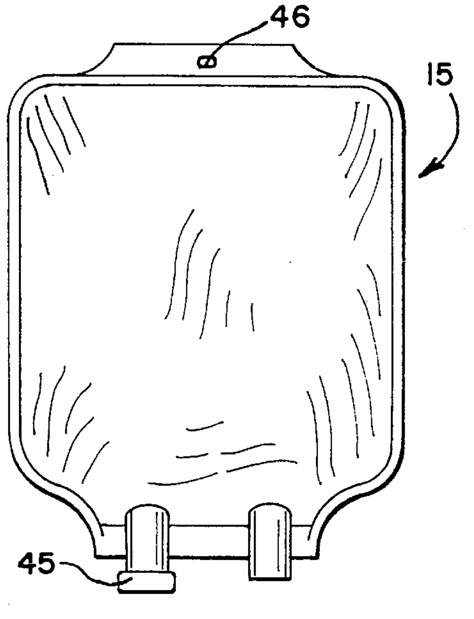
FIG. 6 is a plan view of a receiving container.

The carrier 10, housing four flexible receiving containers 15, may be used in conjunction with a fluid transfer pump 40 as shown in FIG. 4. The solution transfer pump 40 is capable of transferring solutions from separately contained fluid sources, such as supply containers 41, to each of the flexible receiving containers 15 in the carrier 10. The pump 40 has a pump module 42 which houses an internal power supply, motor control board, and load cell circuitry (not shown). The pump module 42 also has a keypad 43 for inputting data and parameters for controlling the pump, including the entry of the desired volume to be delivered to the receiving containers 15. The pump 40 has three pump rotors 44 that are capable of pumping solution from supply containers 41 to each receiving container 15 housed within the carrier 10. Each of the receiving containers 15 has an access port tube 45 at one end and a hanger hole 46 (FIG. 6) at the opposite end of the container 15. Preferably, the receiving containers 15 are placed in the carrier 10 with the access port tube 45 extending through the opening 24 in the carrier 10. This orientation of the receiving containers 15 will allow for the filling of the receiving containers 15 from the top.

Each of the supply containers 41 are fluidly connected with a tubing transfer set 48 to separate fluid inlets 49 associated with each pump rotor 44. The fluid transfer set 48 is sold under the product designation LIFECELL® Transfer Set by Immunotherapy.

Each of the three rotors 44 have fluid outlets 50 which are fluidly connected through separate tubing sets 51 to one end of a transfer set junction 52. The transfer set junction 52 has three fluid inlets 53 and one fluid outlet 54. (This single outlet may be referred to as the pump fluid outlet).

Each of the fluid receiving containers 15 are fluidly connected to the pump 40 fluid outlet 54 with tubing 55. The tubing 55 is divided with a tubing junction 56 having two outlet tubes 57. Each of these outlet tubes 57 are split at a junction 58 to form four fluid supply lines 59. Roll clamps 60 are provided along each supply line 59 so that the receiving containers 15 that are not being filled may be valved off to restrict any fluid flow in or out of the containers 15 not in use.

The carrier 10 is mounted to the pump on a load cell 61 having a load cell arm 62. The load cell 61 has circuitry referred to above that generates a signal that is representative of the weight of the load on the load cell 61. The pump 40 is controlled in response to the weight signal so that a volume of solution pumped to a receiving container 15 may be determined by gravimetrically weighing the carrier 10.

The solution transfer pump 40 is sold under the product designation Solution Transfer Pump by Immunotherapy a Division of Baxter Healthcare code no. 4R4345.

The pump 40 and the carrier 10 may be used in a method for transferring fluids from one fluid source to multiple receiving containers 15 in the carrier 10. The method includes the steps of fluidly connecting a fluid supply container 41 with a transfer set 48 to a pump rotor inlet 49, attaching the carrier 10 to the load cell arm 62, fluidly connecting each of the receiving containers 15 with tubing 59 to the pump outlet 50, providing valves or clamps 60 in each of the supply lines 59 in a closed position, inputting the volume to be delivered on the pump control module 42, entering the specific gravity of the supply fluid into the control module 42, opening the clamp 60 to a first receiving container 15*a*, starting the pump to deliver the desired volume of fluid from the supply into the first receiving container 15*a*. The load cell circuitry sounds an alarm when the desired volume has been delivered. The clamp 60*a* to the first receiving container 15*a* should be closed and the clamp 60*b* to the second receiving container should be opened and the steps followed as set forth above to fill the remaining receiving containers 15*b–d*.

One particular application for this solution transfer method is for the subculturing of cells. The cells may be anchorage dependent or anchorage independent cells. The cells may be hybridomas from which monoclonal antibodies may be obtained by culturing. Alternatively, the cells may be white blood cells such as lymphocytes from a cancer patient. In this circumstance, as it taught in the literature, culturing of the lymphocyte with a lymphokine such as interleukin-2 can provide an activated lymphocyte which is more active in the process of identifying and killing tumor cells. These activated lymphocytes may then be returned to the patient for treatment of the cancer.

The subculturing procedure generally involves the steps of mixing these living cells contained in a first supply container with a cell culture medium contained in a second supply container.

The specific culture medium or media used will be any appropriate type of media desired, depending on the particular cells to be cultured. Many different varieties of media are taught in the prior art. It should also be known that the verb "culture" may refer to the maintenance of cells and their multiplication by growth, but alternatively, it can apply to situations where the cells do not multiply but simply are treated (for example, with a lymphokine) to change their characteristics. One cell medium that may be used for lymphocytes is a medium consisting of RPMI 1640 (low endotoxin; M. A. Bioproducts of Walkersville, Md.) also including 10 units per ml of penicillin, 10 micrograms/ml of streptomycin sulfate, 2 ml. of glutamine, 5 micrograms per ml. of gentamicin, and 2 percent by weight of heat-inactivated human AB serum. This information is disclosed in Rosenberg U.S. Pat. No. 4,690,915. Appropriate media for hybridoma cells are widely available in the literature which include culture media supplemented with animal serum such as bovine or equine serum.

The living cells from the first supply container should be divided equally among the receiving containers 15. For example, if there are four receiving containers 15, you will get a one in four dilution. That is, if you have a 1000 ml initial culture volume, 250 ml will be delivered from the initial cell culture bag to each of the four receiving containers 15, and diluted back to a volume of 1000 ml with 750 ml of fresh culture medium.

The newly divided cells may be transported together in the carrier 10 and placed in an incubator and the culture process continued.

The carrier 10 having the four receiving bags may be connected to the fluid inlet of a single pump rotor inlet 49 and used as a supply container to subculture again.

Another application for this solution transfer method would be for fill procedures in a hospital pharmacy. For example, total parenteral nutrition solutions ("TPN") to be infused four times a day at 1500 ml per infusion may be mixed at one application instead of four using the carrier 10. During the fill sequence various supplemental fluids may be added to the TPN including dextrose, Intralipid (TM) solution, or amino acids.

While specific embodiments have been illustrated and described, numerous modifications are possible without departing from the spirit of the invention, and the scope of protection is only limited by the scope of the accompanying claims.

I claim:

1. An apparatus for holding and carrying a plurality of flexible medical containers comprising:

a rack having a plurality of plates positioned in parallel spaced relation, the plates defining a chamber between each pair of adjacent plates;

a plurality of spacer assemblies each extending through the rack to connect the plates and to maintain the spaced relationship of the plates, the spacer assemblies being spaced along marginal edges of the rack to define two opposed end walls, a bottom, and an opening to the rack to allow access to each of the chambers; and, a means associated with a plate for carrying and suspending the apparatus.

2. The apparatus of claim 1 wherein the plates are generally rectangular in shape.

3. The apparatus of claim 2 wherein there are five plates.

4. The apparatus of claim 3 wherein the plates have a plurality of spaced bores.

5. The apparatus of claim 4 wherein the plates are in registration.

6. The apparatus of claim 1 wherein the spacer assemblies comprise a series of spacer subassemblies each subassembly extending between adjacent plates, each adjacent subassembly being connected together end to end.

7. The apparatus of claim 6 wherein the spacer subassemblies snap fit together.

8. The apparatus of claim 4 wherein the means for carrying the apparatus is a flange extending from a plate having a hanger hole.

* * * * *